(12) United States Patent
Chang et al.

(10) Patent No.: US 7,149,380 B2
(45) Date of Patent: Dec. 12, 2006

(54) THERMALLY INDUCED PRESSURE OPERATED OPTICAL SWITCH AND DISPLAY DEVICE USING THE SAME

(75) Inventors: Jen-Tsorng Chang, Tu-Cheng (TW); Chun-Yu Lee, Tu-Cheng (TW)

(73) Assignee: Hon Hai Precision Industry Co., Ltd. (TW)

( * ) Notice: Subject to any disclaimer, the term of this patent is extended or adjusted under 35 U.S.C. 154(b) by 4 days.

(21) Appl. No.: 11/072,967

(22) Filed: Mar. 4, 2005

(65) Prior Publication Data
US 2006/0120661 A1 Jun. 8, 2006

(30) Foreign Application Priority Data
Mar. 12, 2004 (CN) .............................. 093106644

(51) Int. Cl.
*G02B 6/35* (2006.01)
(52) U.S. Cl. ..................... 385/16; 385/17; 385/18; 385/15; 385/36; 385/901
(58) Field of Classification Search ................ 385/15, 385/16, 17, 18, 12, 13, 14, 129, 130, 131, 385/36, 901
See application file for complete search history.

(56) References Cited
U.S. PATENT DOCUMENTS 4,521,683 A * 6/1985 Miller ..................... 250/221
6,072,924 A * 6/2000 Sato et al. .................. 385/18
6,188,815 B1 * 2/2001 Schiaffino et al. ............ 385/16
6,470,106 B1 10/2002 McClelland et al. .......... 385/16
6,829,079 B1 * 12/2004 Oda et al. ................... 359/318
7,027,683 B1 * 4/2006 O'Connor et al. ............ 385/19

* cited by examiner

*Primary Examiner*—Brian M. Healy
(74) *Attorney, Agent, or Firm*—Morris Manning & Martin LLP; Tim Tingkang Xia, Esq.

(57) ABSTRACT

A thermally induced pressure operated optical switch (3) includes a prism (31), and a substrate (32) disposed below the prism. The substrate defines a plurality of switch elements (35). Each switch element includes a first chamber (351), a second chamber (352) containing matching liquid (36) having a reflective index substantially the same as that of the prism, and a thermal pressure generator (37) communicating with the second chamber for causing the matching liquid to flow between the first and second chambers. The switch elements are arranged in an array in like manner to the way pixels of a display device are arranged. Thus, the thermal pressure generators can be selectively turned on and off, in order to control the switch elements to manipulate optical beams for displaying all kinds of images. The optical switch can be employed in a display device, a projector, or like apparatuses.

22 Claims, 3 Drawing Sheets

THERMALLY INDUCED PRESSURE OPERATED OPTICAL SWITCH AND DISPLAY DEVICE USING THE SAME

BACKGROUND OF THE INVENTION

1. Field of the Invention

The present invention relates to micro switches, and more particularly to thermally induced pressure operated optical switches employed in display devices, projectors or like apparatuses.

2. Prior Art

Micro-Electro-Mechanical Systems, or MEMS, is a rapidly growing technology for the fabrication of miniaturized electronic devices. MEMS employs processes similar to those used in the integrated circuit industry. MEMS technology provides a way to integrate mechanical, fluidic, optical, and electronic functionality in micro-devices, which range in size from 0.1 microns to one millimeter. MEMS devices have two important advantages over conventional counterparts: first, like integrated circuits, they can be fabricated in large numbers, so that the cost of production can be reduced substantially; second, they can be directly incorporated into integrated circuits, so that far more complicated systems can be made than with other technologies.

In certain kinds of MEMS devices, fluid can be moved through the MEMS device by the growing and collapsing of vapor bubbles. A vapor bubble is formed in each of cavities by an imbedded resistive heater. The cavity is connected to a nozzle on one side and a diffuser on the other, so that the cavity preferentially biases flow of the fluid from the nozzle to the diffuser. In practice, a bubble is periodically nucleated in the chamber, and the bubble pushes fluid from the chamber. Subsequently, the bubble collapses and pulls fluid back into the chamber. Both the expansion and the collapse are supposed to result in a net flow of the fluid from the nozzle to the diffuser.

Taiwan Pat. No. 503,332, issued on Sep. 21, 2002, discloses a reflection type optical switch employing a thermal bubble ink-jet printing apparatus and working fluid. The optical switch is represented in FIG. 7 hereof with the reference numeral 2. A detailed explanation of the configuration of the optical switch 2 is provided hereinbelow.

The optical switch 2 includes a transparent polygonal cylinder 21, a plurality of coupling glasses 23, working fluid 25, and pushing devices 27. The polygonal cylinder 21 has a plurality of side surfaces 212. The coupling glasses 23 are located adjacent to the side surfaces 212 respectively, to form a plurality of slits 232 between the coupling glasses 23 and the side surfaces 212. The working fluid 25 is contained in the slits 232. The working fluid 25 has a reflective index the same as that of the polygonal cylinder 21 and the coupling glasses 23.

The pushing devices 27 are thermal bubble ink-jet printing apparatuses, and each of them includes an imbedded heater (not labeled). When the heater is turned on, a vapor bubble 271 is created in the corresponding slit 232. By continuing to heat the vapor bubble 271, it expands to push the working fluid 25 out of the slit 232. When the heater is turned off, the temperature of the vapor bubble 271 decreases. The vapor bubble 271 collapses, and the working fluid 25 is pulled back into the slit 232 again.

In operation, an optical beam is directed into the transparent polygonal cylinder 21. When the optical beam transmits to a side surface 212 where the working fluid 25 has been push out from the corresponding slit 232, the optical beam is totally reflected. When the optical beam transmits to a side surface 212 where the working fluid 25 is contained in the corresponding slit 232, the optical beam totally passes through. The optical switch is used in optical fibers, to dynamically reconfigure the interconnection of optical beam paths. This is done by thermally controlling the presence or absence of working liquid in a slit at which a plurality of coupling glasses is located. Alternatively, the slit may be located where other kinds of optical waveguide segments intersect.

However, the above-described optical switch is generally limited in application, and does not manipulate light for viewing by humans.

SUMMARY OF THE INVENTION

An object of the present invention is to provide a thermally induced pressure operated optical switch that can be employed in a display device.

In order to achieve the object set out above, a thermally induced pressure operated optical switch in accordance with the present invention includes a prism, and a substrate disposed below the prism. The substrate defines a multiplicity of switch elements. Each switch element comprises a first chamber, a second chamber containing matching liquid having a reflective index substantially the same as that of the prism, and a thermal pressure generator communicating with the second chamber for causing the matching liquid to flow between the first and second chambers. The switch elements are arranged in an array in like manner to the way pixels of a display device are arranged. Thus, the thermal pressure generators can be selectively turned on and off, in order to control the switch elements to manipulate optical beams for displaying all kinds of images. The optical switch can be employed in a display device, a projector, or like apparatuses.

Other objects, advantages, and novel features of the present invention will become more apparent from the following detailed description when taken in conjunction with the accompanying drawings.

DETAILED DESCRIPTION OF THE INVENTION

Reference now will be made to the drawings to describe the present invention in detail.

Figure 1:
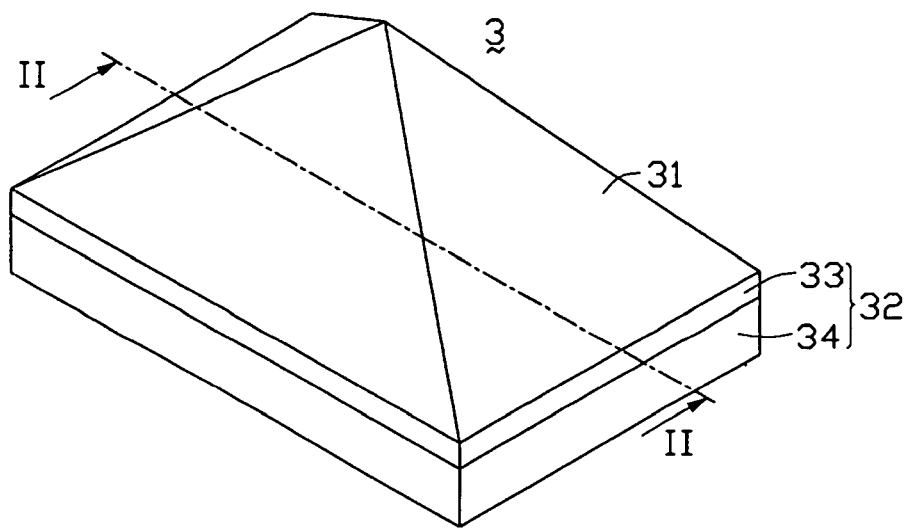
FIG. 1 is an isometric view of an optical switch according to the present invention.

FIG. 1 is an isometric view of a thermally induced pressure operated optical switch 3 according to the present invention. The optical switch 3 includes a pyramidal prism 31, and a substrate 32 mating with a base surface of the prism 31. The prism 31 is made of glass material, which has a reflective index equal to or greater than 1.4. The substrate 32 includes an upper layer 33 and a lower layer 34.

Figure 2:
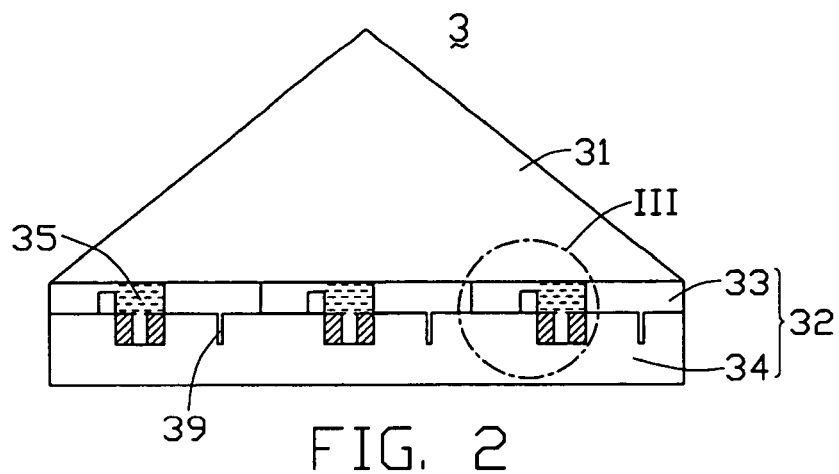
FIG. 2 is a schematic, side cross-sectional view taken along line II—II of FIG. 1, showing the optical switch in a closed state.

FIG. 2 is a schematic, side cross-sectional view of the optical switch 3. The substrate 32 defines a multiplicity of switch elements 35 arranged in a regular array. The substrate 32 further includes a plurality of thermal isolated grooves 39 disposed between every two adjacent switch elements 35, to prevent heat transferring between the switch elements 35.

Figure 3:
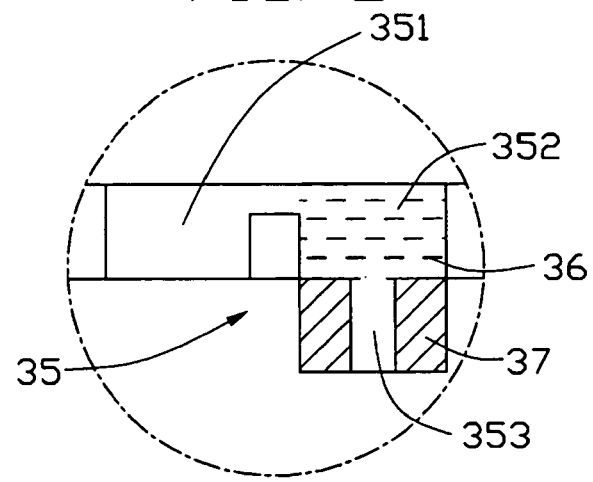
FIG. 3 is an enlarged view of a circled portion III of FIG. 2, showing matching liquid contained in a second chamber.

FIG. 3 is an enlarged view of a switch element 35 in a closed state. The switch element 35 includes two chambers 351, 352 contained in the upper layer 33, matching liquid 36 containing in the chamber 352, and a thermal pressure generator 37 contained in the lower layer 34 below the chamber 352. The chambers 351, 352 communicate with each other. The chamber 351 defines an opaque region at a surface of the upper layer 33 thereabove, said surface abutting the prism 31. The chamber 352 defines a transparent region at a surface of the upper layer 33 thereabove, said surface abutting the prism 31. The matching liquid 36 is an organic solvent, which has a reflective index substantially the same as that of the prism 31.

The thermal pressure generator 37 is a kind of thermal bubble generator similar to that used in inkjet printing apparatuses. The thermal pressure generator 37 includes a chamber 353, which communicates with the chamber 352. The thermal pressure generator 37 further includes a heater (not labeled) and a condenser (not labeled).

Figure 4:
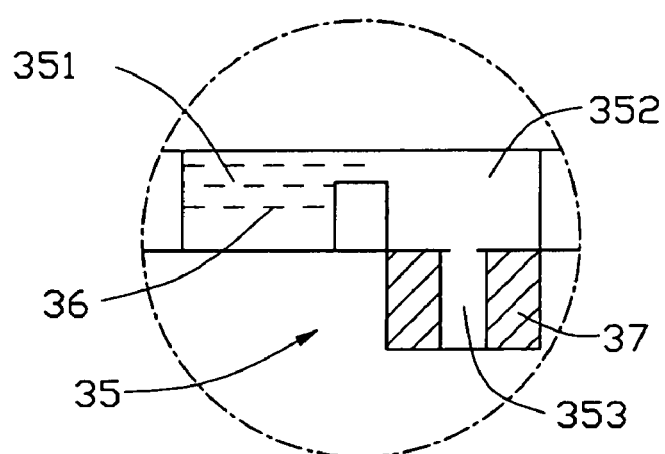
FIG. 4 is similar to FIG. 3, but showing the matching liquid contained in a first chamber when the optical switch in an open state.

FIG. 4 is an enlarged view of the switch element 35 in an open state, which is obtained by the matching liquid 36 being pushed from the chamber 352 to the chamber 351 by a thermal bubble created by the thermal pressure generator 37. Operating the thermal pressure generator 37 to open the switch element 35 includes the steps of: turning on the thermal pressure generator 37 to form the thermal bubble in the chamber 353; and heating and expanding the thermal bubble to push the matching liquid 36 out of the chamber 352. Once the open state is reached, heating of the thermal bubble is maintained so that the switch element 35 is held in the open state. When the heating is stopped, the thermal bubble collapses in a short time, the matching liquid is pulled back into the chamber 352, and the switch element 35 returns to the closed state. The condenser can help to accelerate the collapse of the thermal bubble.

Figure 5:
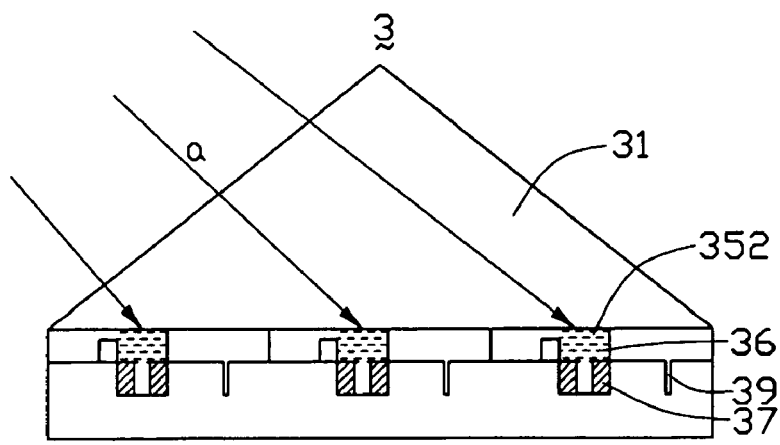
FIGS. 5–6 are essential optical path diagrams of the optical switch shown in FIG. 2, respectively showing the optical switch in a closed state and in an open state.
Figure 6:
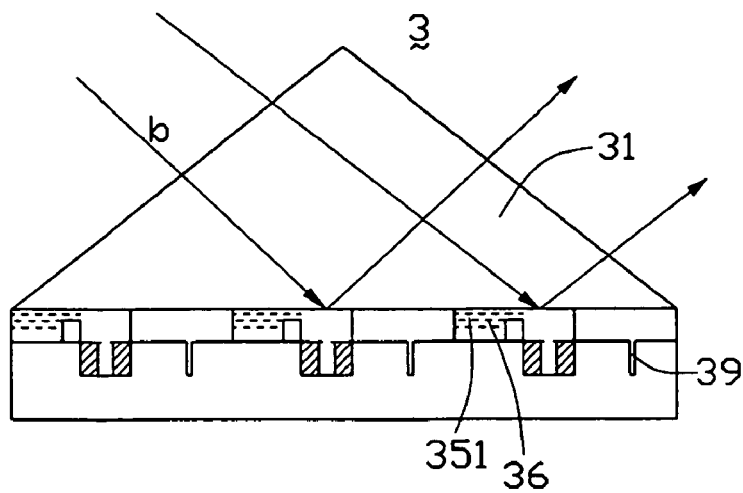
Figure 7:
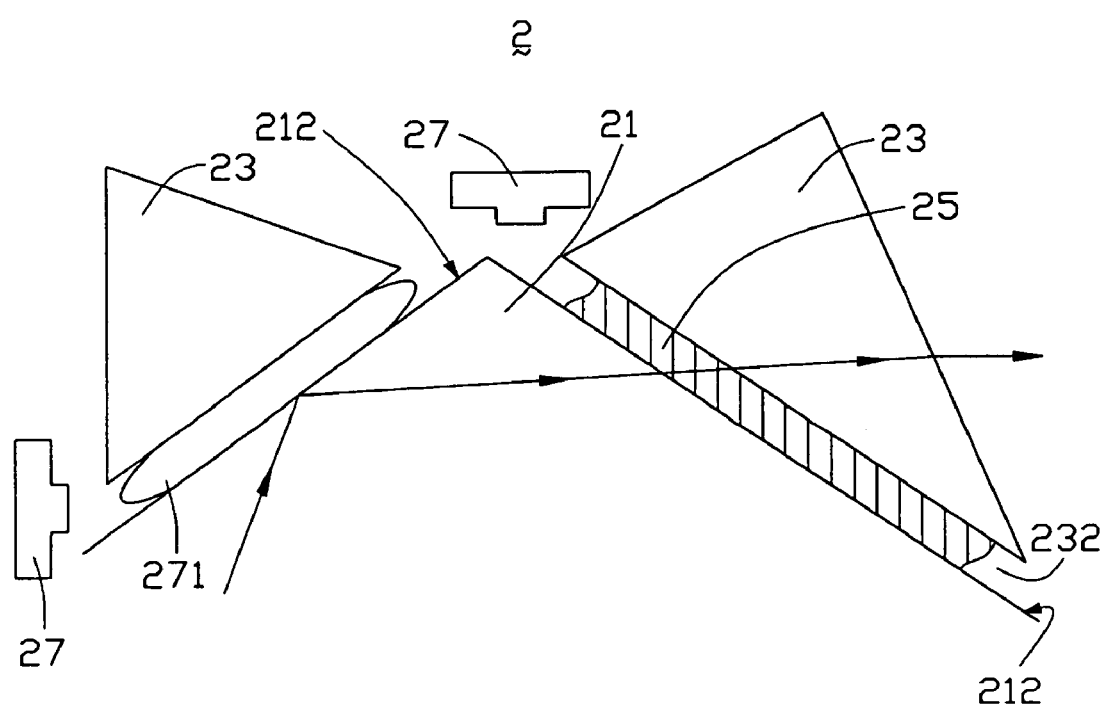
FIG. 7 is a schematic, cross-sectional view of a conventional reflection type optical switch employing a thermal bubble ink-jet printing apparatus.

The optical switch 3 can be employed in a display device. FIGS. 5–6 are essential optical paths diagrams of the optical switch 3 used in the display device. As shown in FIG. 5, in operation, all the thermal pressure generators 37 are turned off, and the switch elements 35 are in a closed state. When an optical beam 'a' is directed in through the prism 31, part of the optical beam 'a' is absorbed by the opaque region of a corresponding switch element 35, and a residue of the optical beam 'a' passes through the matching liquid 36. No part of the optical beam 'a' is reflected back into the prism 31 to subsequently illuminate the display. Thereby, the display device shows a black display.

On the other hand, as shown in FIG. 6, when all the thermal pressure generators 37 are turned on, the switch elements 35 are in an open state, the matching liquid 36 is in the chambers 351, and the thermal bubbles are in the chambers 352. When an optical beam 'b' is directed in through the prism 31, part of the optical beam 'b' is absorbed by the opaque region of the corresponding switch element 35, and a residue of the optical beam 'b' is totally reflected at the transparent region of the switch element 35 because the thermal bubble has a reflective index less than that of the prism 31. The residue of the optical beam 'b' passes through the prism 31 to subsequently illuminate the display. Thereby, the display device shows a white display.

The switch elements 35 are arranged in the array in like manner to the way pixels of a display device are arranged. Thus, the thermal pressure generators 37 can be selectively turned on and off, in order to control the switch elements 35 to manipulate optical beams for displaying all kinds of images.

Many modifications and variations are possible within the ambit of the invention herein. For example, the optical switch 3 can define a multiplicity of pixels, with each pixel including a plurality of switch elements 35. When the optical switch 3 is employed in a display device, gray scales can be displayed by controlling the extent of opening of the switch elements 35 in each pixel.

Moreover, the prism 31 can be replaced with a plurality of micro prisms arranged in a regular array, with each micro prism corresponding to one of the switch elements 35.

Furthermore, the matching liquid 36 can be ink or a like substance, which has a reflective index substantially the same as that of the prism 31.

The optical switch 3 can be employed in a display device, projector, or like apparatuses. It is conveniently to selectively operate the thermal pressure generators 37 to open or close each switch element 35 in each pixel. The display device employing the optical switch 3 can even display color images by employing a color filter, a color wheel or other color devices.

It is to be understood, however, that even though numerous characteristics and advantages of the present invention have been set out in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An optical switch, comprising:
   a prism portion; and
   a substrate below the prism portion, the substrate defining a plurality of switch elements, each switch element comprising:
   a first chamber;
   a second chamber containing matching liquid having a reflective index substantially the same as that of the prism portion; and
   a thermal pressure generator communicating with the second chamber, for causing the matching liquid to flow between the first and second chambers.

2. The optical switch as claimed in claim 1, wherein the prism portion has a reflective index equal to or greater than 1.4.

3. The optical switch as claimed in claim 2, wherein the prism portion is a pyramidal prism.

4. The optical switch as claimed in claim 2, wherein the prism portion comprises an array of micro prisms, and each micro prism is disposed corresponding to a respective one of the switch elements.

5. The optical switch as claimed in claim 1, wherein the matching liquid is an organic solvent.

6. The optical switch as claimed in claim 1, wherein the matching liquid is ink.

7. The optical switch as claimed in claim 1, wherein the first chamber and the second chamber communicate with each other.

8. The optical switch as claimed in claim 7, wherein the first chamber defines an opaque region for absorbing optical beams directed thereto.

9. The optical switch as claimed in claim 8, wherein the second chamber defines a transparent region for reflecting optical beams thereat.

10. The optical switch as claimed in claim 1, wherein the thermal pressure generator comprises a chamber communicating with the second chamber.

11. The optical switch as claimed in claim 10, wherein the thermal pressure generator forms a thermal bubble in its chamber.

12. The optical switch as claimed in claim 11, wherein the thermal pressure generator further comprises a heater for heating the bubble.

13. The optical switch as claimed in claim 11, wherein the thermal pressure generator further comprises a condenser for cooling the bubble.

14. The optical switch as claimed in claim 1, wherein the substrate further defines a plurality of thermal isolation grooves between adjacent switch elements.

15. A display device, comprising:
a prism portion; and
a substrate defining a plurality of pixel units below the prism portion, each pixel unit comprising:
a first chamber;
a second chamber containing matching liquid having a reflective index substantially the same as that of the prism portion; and
a thermal pressure generator communicating with the second chamber, for causing the matching liquid to flow between the first and second chambers.

16. The display device as claimed in claim 15, wherein the prism portion has a reflective index equal to or greater than 1.4.

17. The display device as claimed in claim 16, wherein the prism portion is a pyramidal prism.

18. The display device as claimed in claim 16, wherein the prism portion comprises an array of micro prisms, and each micro prism is disposed corresponding to a respective pixel unit.

19. The display device as claimed in claim 15, wherein the first chamber and the second chamber communicate with each other.

20. The display device as claimed in claim 19, wherein the first chamber defines an opaque region, and the second chamber defines a transparent region.

21. A method for illuminating in a display device, comprising:
providing a predetermined light path in said display device to illuminate by means of passage of light through said light path;
interferingly setting at least one pixel unit having a first chamber and a second chamber in communication with each other in said light path;
placing vaporizable liquid in said second chamber so as to allow said light to pass through said liquid rather than along said light path; and
selectively thermally generating pressure to urge said liquid moving toward said first chamber so as to reflect said light at said second chamber back to said light path.

22. The method as claimed in claim 21, wherein a vapor bubble is thermally created to occupy said second chamber in order for urging said liquid to flow into said first chamber in said thermally-generating step.

* * * * *